(12) United States Patent
Hell

(10) Patent No.: US 7,064,824 B2
(45) Date of Patent: Jun. 20, 2006

(54) HIGH SPATIAL RESOULUTION IMAGING AND MODIFICATION OF STRUCTURES

(75) Inventor: Stefan Hell, Göttingen (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 184 days.

(21) Appl. No.: 10/420,896

(22) Filed: Apr. 22, 2003

(65) Prior Publication Data

US 2004/0212799 A1    Oct. 28, 2004

(30) Foreign Application Priority Data

Apr. 13, 2003    (DE) ................................ 103 17 613

(51) Int. Cl.
*G01J 3/30* (2006.01)
(52) U.S. Cl. .................... 356/317; 356/318; 250/458.1
(58) Field of Classification Search ................ 356/317, 356/318; 250/458.1, 459.1; 435/4–6
See application file for complete search history.

(56) References Cited

U.S. PATENT DOCUMENTS

| | | | |
|---|---|---|---|
| 6,555,826 B1 | 4/2003 | Hoffmann | 250/458.1 |
| 6,844,150 B1 * | 1/2005 | Weiss et al. | 435/4 |
| 2002/0057430 A1 * | 5/2002 | Engelhardt | 356/318 |
| 2002/0179828 A1 * | 12/2002 | Engelhardt et al. | 250/234 |

FOREIGN PATENT DOCUMENTS

| | | |
|---|---|---|
| WO | WO 95/21393 | 8/1995 |
| WO | PCT/DE95/00124 | 10/1995 |

OTHER PUBLICATIONS

Klar et al, Subdiffraction resolution in far-field fluorescence microscopy, Jul. 15, 1999, vol. 24, No. 14, pp. 954-956.*
Accelerated Publication, "Natural Animal Coloration Can Be Determined by a Nonfluorescent Green Fluorescent Protein Homolog," p. 25879, Jun. 13, 2000.
Nature Publishng Group, A Digital Fluorescent Molecular Photoswitch, p. 759-760, Dec. 2002.

(Continued)

*Primary Examiner*—Layla G. Lauchman
(74) *Attorney, Agent, or Firm*—Thomas, Kayden, Horstemeyer & Risley, LLP

(57) ABSTRACT

In a method of high spatial resolution imaging or modifying a structure, the structure is marked with a substance which is selected from the group of substances which can be transferred from a first state having first optical properties to a second state having second optical properties by means of an optical switch over signal. Then, the second state of the substance is adjusted with the switch over signal except for a spatially limited area. If the substance and the switch over signal are adapted to each other in such a way, that everywhere where the switch over signal exceeds a threshold value essentially the second state of the substance is adjusted, and if the spatial area purposefully omitted by the switch over signal is an intensity minimum of an interference pattern, the spatial area of the structure in which the substance is within the first state becomes smaller than the diffraction limit for the switch over signal.

72 Claims, 1 Drawing Sheet

OTHER PUBLICATIONS

Accelerated Publication, "Natural Animal Coloration Can Be Determined by a Nonfluorescent Green Fluorescent Protein Homolog," p. 25879-25882, Jun. 13, 2000.

"On/Off Blinking and Switching Behavior of Single Molecules of Green Fluorescent Protein" by Robert M. Dickson, Andrew B. Cubitt, Roger Y. Tsien, and W. E. Moerner, Nature/vol. 388/Jul. 24, 1997, p. 355-358.

Physical Review Letters, vol. 88, 2002, Marcus Dyba dn Stefan W. Hell, pp. 163901-1-163901-4.

Topics in Fluoreszence Spectroscopy, vol. 5: Incresing the Resolution of Far-Field Fluorescence Light Microscopy by Point-Spread-Function Engineering, by Stefan W. Hell, 1997, pp. 361-426.

* cited by examiner

HIGH SPATIAL RESOULUTION IMAGING AND MODIFICATION OF STRUCTURES

FIELD OF THE INVENTION

This invention relates to a method of high spatial resolution imaging a structure of a sample, comprising a substance having at least two different states, especially of a biologic sample, the method comprising the steps of changing the state of the substance with an optical switch over signal which purposefully omits at least one spatial area, and registering an optical measurement signal from at least one of the spatial areas purposefully omitted by the switch signal.

Further, the invention relates to a method of high spatial resolution modification of an optical structure, especially the content of an optical data storage or the photosensitive layer of a substrate which is to be changed microlithographically, the method comprising the steps of providing a structure consisting of the substance having special optical properties and changing an optical state of the substance in a spatially limited area by means of an optical writing signal. The structure made of the substance may include a plane layer, i.e. a film, but also a larger thee dimensional volume of the substance. Such a method can also be used for microlithographically producing nanostructures, for example for producing integrated circuits or other nanodevices.

At last, the invention also relates to an optical data storage having a structure made of a substance having special optical properties, an optical state of the substance being changeable within a spatially limited area by means of an optical writing signal.

DESCRIPTION OF RELATED ART

The spatial resolution both of imaging and modifying optical methods is in principle set by the diffraction limit (Abbe's limit) at the respective wave length.

In the field of fluorescence microscopy, however, methods are already known in which, in imaging a structure of a sample, the resolution is effectively made higher than the diffraction limit by using a non-linear relationship between the sharpness of the definition of the effective focal spot and the input intensity. Examples are the multiphoton absorption in a sample and the generation of higher harmonics of the input light. Very effective methods which use such a non-linear relationship are the stimulated emission depletion (STED) of the fluorescent state, and the ground state depletion (GSD). These method can in principle achieve a molecular resolution.

Both methods include that, by means of these non-linear relationships, a fluorescence dye by which the structure of interest of a sample is marked is transferred to an energy state from which no fluorescence is (still) possible everywhere where an optical switch over signal exceeds a threshold value. If the spatial area from which a measurement signal is still registered is defined by an intensity minimum of an interference pattern, its dimensions, and thus the achieved spatial resolution, are smaller than the diffraction limit. The non-linear relationship is the saturation of the light induced switch over process.

A STED method having the features of the preamble of claim 1 is known from WO 95/21393 A1. In this method, a sample or a fluorescence dye in the sample is excited for fluorescence by means of an exciting beam. The spatial area of the excitation, to which the diffraction limit normally applies, is then reduced in that it is superimposed with an intensity minimum of an interference pattern of an stimulation beam as a switch over signal. Everywhere, where the switch over signal exceeds an saturation threshold value, the fluorescence dye is fully stimulated for stimulated emission, i.e. it is brought down from the previously excited energy state. The remaining spatial area from which afterwards fluorescence light is still spontaneously emitted only correspond to a reduced area around the center of the intensity minimum in which the switch over signal was not present or not present with a sufficient intensity. Although this method of fluorescence microscopy obviously provides a spatial resolution below the diffraction limit it also has disadvantages. The life time of the energy state of the fluorescence dye excited by the exciting beam is only short. Thus, a comparatively high intensity of the switch over signal has to be applied for effectively completing the switching over within the short period of time. The intensity of the stimulation beam has additionally to be very high so that the stimulation by the switch over signal shows a non-linear relationship between the remaining fluorescence and the intensity of the switch over signal, i.e. so that saturation is achieved. Thus, as a rule, a pulsed high power laser is necessary for the stimulation light beam, which makes the application of the known method quite cost-intensive.

These disadvantages also apply to known GSD methods as time limitations and power requirements are here also set by short life times of the involved energy states.

From The Journal of Biological Chemistry, Vol. 275, No. 84, pages 25879–25882 (2000) a protein is known which can increasingly be excited for fluorescence in a red range by means of green light, which, however, looses its fluorescence properties upon exposition to blue light. This process is reversible. It looks like that the green light switches the protein to a conformational state in which it has the fluorescence property, and at the same times excites the fluorescence, whereas the blue light switches the protein to a conformational state without the fluorescence property. The protein is a protein naturally occurring in the sea anemone *anemonia sulcata*, the functions of which described here may be purposefully enhanced by exchanging one amino acid. It is also known from Nature Vol. 388 pages 355–358 (1997) that the green fluorescent protein (GFP) and mutants thereof may be switched between two states one of which differs from the other in a spectral aspect. Both proteins can be used as fluorescence markers in a living cells.

From Nature, Vol. 420 pages 759–760 (2002) fluorescent molecules from the family of diarylethenes are known which may be deliberately switched between a fluorescent and a non-fluorescent state. Both states are thermally stable so that the switching process can be effected with comparatively low intensities. In this case, the switching process is a photoisomerization. Such molecules can also be denoted as photochromic.

In a method of high spatial resolution modifying an optical structure the diffraction limit is the natural limit for the resolution, for example in writing data into an optical data storage and thus for the data density obtainable within the data storage. The same applies to microlithography: for producing smaller and smaller structures, for example within a photo resist, smaller and smaller wave lengths have to be used up to now. Presently, deep-UV-light is used, X-ray light is tested for the future. The problem here is, that light with a wave lengths <250 nm is not easily focused, and the optics to be used become expensive and inefficient.

BRIEF SUMMARY OF THE INVENTION

According to one aspect, the invention provides a method of high spatial resolution imaging a structure of a sample comprising a substance with at least two different states, particularly of a biological sample, the method comprising the steps of changing the state of the substance with an optical switch over signal which purposefully omits at least one spatial area, and registering an optical measurement signal from at least one area purposefully omitted by the switch signal, the substance being selected from the group of substances which may repeatedly be transferred from a first state having first spectral properties to a second state having second spectral properties by means of the switch over signal, and which may return from the second state to the first state, the optical measurement signal being essentially generated by such parts of the substance which have the first and not the second spectral properties.

According to a further aspect, the invention provides a method of high spatial resolution modifying an optical structure, particularly the content of an optical data storage or the photosensitive layer of a substrate which is to be changed microlithographically, the method comprising the steps of providing a structure consisting of a substance having special optical properties, and changing an optical state of the substance within a spatially limited area by means of an optical writing signal, the substance being selected from the group of substances which may repeatedly be transferred from a first state having first optical properties to a second state having second optical properties by means of an optical switch over signal, and which may be returned from the second state to the first state, the spectral state of the substance being changeable by means of the optical writing signal in the first state only, and the second state of the substance being set by means of the switch over signal except for the spatially limited area.

According to a further aspect, the invention provides an optical data storage having a structure made of a substance having special optical properties, one optical state of the substance being changeable in a spatially limited area by means of an optical writing signal, the substance belonging to the group of substances which may repeatedly be transferred from a first state with first optical properties to a second state with second optical properties, and which may be returned from the second state to the first state, the optical properties of the substance being changeable by the optical writing signal in the first state only.

BRIEF DESCRIPTION OF THE DRAWINGS

In the following the invention is further explained and described by means of details shown in the drawing.

DETAILED DESCRIPTION OF THE INVENTION

Figure 1:
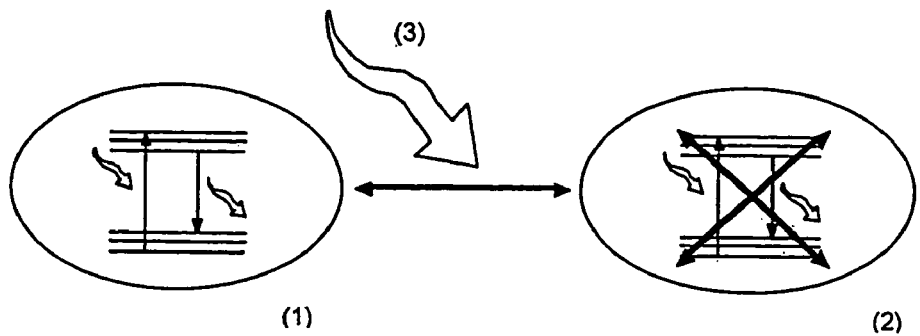
FIG. 1 symbolically shows two conformational states of a molecule or a molecule complex, and FIG. 2 schematically shows a device for carrying out the invention.

Using substances having two states with different optical properties is a common feature of all aspects of the invention. Further, the substance can purposefully be switched with a switch over signal from the first to the second state. This process is reversible. I.e. the substance can also be returned to the first state. The optical properties of the substance in the first state differ from those in the second state in that only they support the measurement signal or the writing signal, respectively. However, it is not necessary that the relevant optical properties are "binary", i.e. it is not necessary that they are present in the one state at 100% and in the other state at 0%. Instead, it is sufficient, if the relevant optical properties show such big differences that at least an essential association of the measurement signal or the writing signal, respectively, to the first state is possible. These states can be two different conformational states of a molecule or a molecule group. Different arrangements of atom groups, photo-induced cis-trans-isomerizations, protonations/de-protonations, spinflip, electron transfer and energy transfer between connected molecules or molecule subunits are possible here.

With regard to the state of the art in the field of fluorescence microscopy, the big advantage of the invention is that the states of the possible substances have a life time which is several times longer than the energy states involved in fluorescence which do not change the spectral properties of the respective substance as such. Further, the intensities which are necessary for achieving a conformational change are comparatively small. Switch over processes in which the start and/or the end state are quite long lived (>100 ns) can be effected with comparatively small intensities—the longer the life time of the states the smaller the required intensity.

Preferably, such substances are used in the new method which can be transferred from the second to the first state by means of another switching signal. The other switching signal may be an optical signal like the switch over signal. It may, however, also be an electric or thermal signal, for example. Further, it is possible, that switching back to the first state occurs spontaneously, i.e. only thermally driven. It is known, for example, that molecules which undergo a photo-induced cis-trans-isomerisation can simply thermally return to the first state. By means of the other switching signal the substance can, however, be purposefully returned to the first state, which may be an advantage in accelerating the procedure.

The other switching signal is preferably applied prior to the switch over signal. If switching with the switch over signal is not affected by the other switching signal, the other switching signal may also be applied during application of the switch over signal to the sample. It is often also not necessary to limit the other switching signal to the spatial area of interest. The spatial limitation which is necessary for increasing the resolution is achieved by the switch over signal.

In the field of high resolution imaging, the present invention is not limited to fluorescence microscopy. Other processes effecting a light emission of a sample can also be used, and even further optical properties are useable which change with the state of the substance marking the structure of the sample. An example for this is a different absorption of a probe beam. Further examples are the polarization of the emitted or absorbed light and its wave length.

If the measurement signal is some light emitted by the sample, a corresponding excitation signal should be applied after and/or during application of the switch over signal to the sample. In any case it should be applied to the sample later or at least not earlier than at the same time as the other switching signal, so far as the excitation signal and the other switching signal are not identical anyway.

For fully imaging a sample it is required to scan the sample with the areas purposefully omitted by the switch over signal. In this case, the sample may at one point of time be simultaneously measured with regard to the measurement signal in a plurality of separated points, i.e. a plurality of spatially limited areas. Scanning can be effected by moving the switch signals used, particularly the switch over signal, with regard to the coordinates of the sample.

Preferable, all spatial areas purposefully omitted by the switch over signals are intensity minima of an interference pattern. In this case, scanning can be effected by moving one or a plurality of interference minima of the switch over signal. Thus, the movement can be achieved by a simple phase shift of the interfering beams. In principle, projections can also be used; the switch over signal can also be applied from the side at a small or blunt angle. Further, holograms are possible. Intensity minima of simple interference patterns, however, enable to define smallest spatial areas, which are avoided by the switch over signal, in a particular simple way.

This is of particular interest, if it is intended to surpass the diffraction limit in imaging. To this end, the substance and the switch over signal are to be adapted to each other so that the transfer from the first state to the second state by means of the switch over signal is non-linearly correlated with the intensity of the switch over signal so that the transfer of the substance to the second state is effected to the most possible extend everywhere where the switch over signal exceeds a threshold value. I.e. the saturation of the change of state has to be achieved everywhere outside of the intensity minimum of the interference pattern.

Preferably, the substance with the special optical properties is selected from the group of proteins. This group particularly includes the known proteins asCP (asSP595) and T70A/A148S/S165V which have two conformational states with suitable optical properties, and also the green fluorescent protein (GFP) and mutants derived thereof. Proteins as marker substances can also be introduced into a biological sample by genetic engineering so that no subsequent staining of the sample is required which affects the sample or which alters the sample at least by staining. The sample can also intrinsically have molecules with suitable optical states.

After marking the structure with the fluorescent substance, the new imaging method can be carried out on a usual fluorescence microscope, the additional efforts for enhancing the resolution below the diffraction barrier being comparatively small and may be limited to means for providing the optical switch over signal. These means can, for example, comprise a simple laser or even a conventional lamp. In a preferred embodiment in which several areas are simultaneously measured for accelerating the method, the measurement signals from the individual areas are simultaneously read by a (CCD-)camera. The full image of the sample results from putting together a plurality of images with different positions of the measured areas in the sample.

In the new method of high spatial resolution modification of an optical structure, the substance having the special optical properties has to be selected so that it is only transferred in one of two states by means of the writing signal to another optical state which, for example has a particular high absorption. This optical state is no energy state like in case of fluorescence but a remaining change of the chemistry of the substance, for example. The change can be irreversible or reversible. If it is reversible, its reversion should neither be effected by the switch over signal nor any other signal used for the original change.

Using all possibilities of the present invention, the new method can be used to write into an optical data storage with a particularly high data density which is no longer limited by the diffraction limit. In the same way, micro- or even nanostructures can be written or formed.

FIG. 1 symbolically shows a molecule or a molecule complex which can be in two different states (1) and (2). One of the states is fluorescent. The other (2) is not. By means of illuminating with a characteristic wave length (3) a purposeful change between the states can be induced. The molecule may also spontaneously return from the second state.

Figure 2:
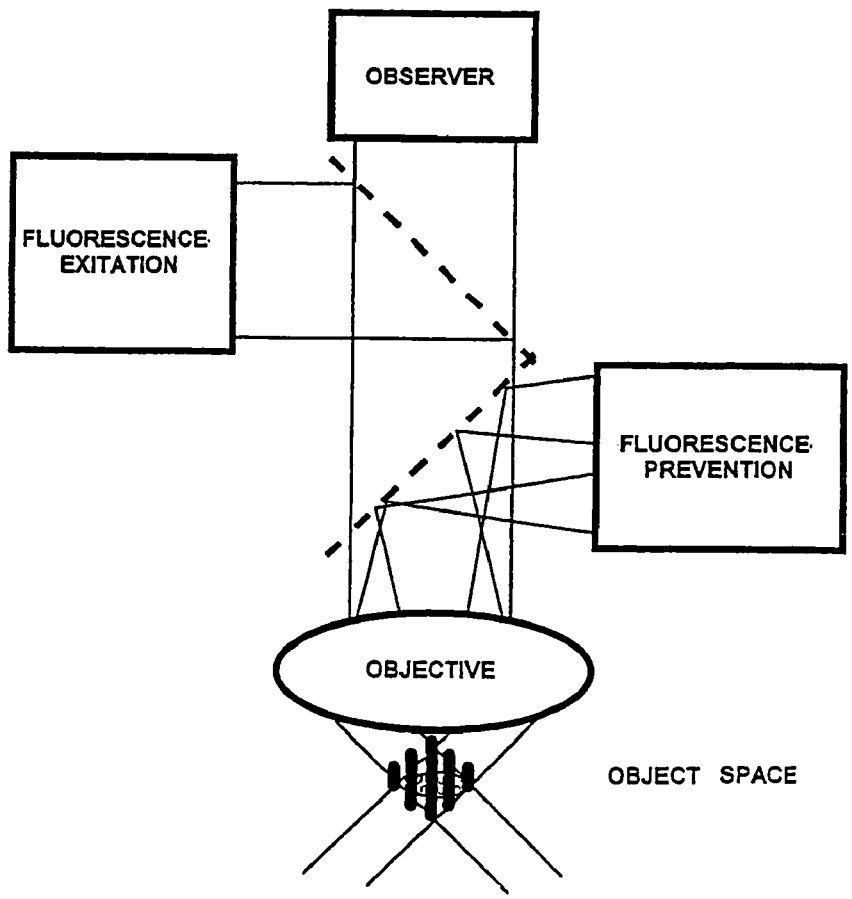

FIG. 2 schematically shows a suitable device for carrying out the invention. A sample (object) is here, on the one hand, excited for fluorescence by an excitation signal from a fluorescent excitation; on the other hand, it is hindered from fluorescence at defined points by means of a switch over signal in that molecules are reversibly brought into a non fluorescent state depending on their position. In the example shown, this is effected by superimposed interfering beams. Thus, fluorescence can only be produced in small gaps which, under suitable conditions, such as a saturation of the switch over process, are smaller than the diffraction limit. By means of a scanning movement of the pattern and sequentially detecting and reading out the fluorescence with a camera, the whole object can be imaged with high resolution.

Although a preferred embodiment of the invention has been disclosed in detail herein, it will be obvious to those skilled in the art that variations and modifications of the disclosed embodiment can be made without departing from the spirit and scope of the invention as set forth in the following claims.

The invention claimed is:

1. A method of high spatial resolution imaging a structure of a sample comprising a substance having at least two different states, the method comprising the steps of:
   changing the state of the substance by means of an optical switch over signal, which purposefully omits at least one spatial area, and
   detecting an optical measurement signal from at least one of the spatial areas purposefully omitted by the switch signal, the substance being selected from a group of substances which is capable of being repeatedly transferred from a first state having first spectral properties to a second state having second spectral properties by means of the switch over signal and which is capable of returning from the second state to the first state, the optical measurement signal being essentially generated by such portions of the substance which have the first but not the second spectral properties,
   wherein the first spectral properties as compared to the second spectral properties comprise a distinguishing feature which is selected from:
   an increased optical absorption of a probe beam;
   an altered polarization property for a probe beam; and
   an increased luminescence selected from the group including fluorescence, phosphorescence, electro-luminescence and chemo-luminescence.

2. The method of claim 1, wherein the two states are different conformational states of a molecule or a molecule group.

3. The method of claim 1, wherein the substance is selected from the group of substances which may be transferred from the second state to the first state by means of another switching signal.

4. The method of claim 3, wherein the other switching signal is applied to the sample prior to the switch over signal.

5. The method of claim 3, wherein the other switching signal is applied to the sample across all areas which are covered by or purposefully omitted by the switch over signal.

6. The method of claim 1, wherein the first spectral properties as compared to the second spectral properties comprise an increased luminescence selected from the group including fluorescence, phosphorescence, electro-luminescence and chemo-luminescence, and wherein an excitation signal is applied to the sample after the switch over signal.

7. The method of claim 6, wherein the excitation signal is applied to the sample across all areas which are covered or purposefully omitted by the switch over signal.

8. The method of claim 1, wherein the first spectral properties as compared to the second spectral properties comprise an increased luminescence selected from the group including fluorescence, phosphorescence; electro-luminescence and chemo-luminescence, and wherein the luminescence is excited by the other switching signal, the other switching signal being applied to the sample during the application of the switch over signal.

9. The method of claim 1, wherein the sample is scanned with the areas purposefully omitted by the switch over signal.

10. The method of claim 1, wherein all spatial areas purposefully omitted by the switch over signal are intensity minima of an interference pattern.

11. The method of claim 1, wherein the substance and the switch over signal are adapted to each other so that everywhere, where the switch over signal exceeds a threshold value essentially the second state of the substance is adjusted.

12. The method of claim 11, wherein the substance and the switch over signals are adapted to each other so that in transfer from the first state to the second state by means of the switch over signal a saturation of the transfer is achieved.

13. The method of claim 1, wherein the substance is selected from the group of substances which includes proteins.

14. The method of claim 1, wherein the substance is selected from the group of substances which includes fluorescent proteins.

15. The method of claim 14, wherein the substance is selected from the group of substances, which includes asCP (asFPS95), green-fluorescent protein (GFP), T70a/A148S/S165V an mutants thereof.

16. The method of claim 14, wherein the substance is introduced into a biological sample for marking its structures in an genetic engineering way.

17. The method of claim 1, wherein the method is carried out on a fluorescence microscope after marking the structures with the substance.

18. A method of high spatial resolution imaging a structure of a sample comprising a substance having at least two different states, the method comprising the steps of
changing the state of the substance by means of an optical switch over signal, which purposefully omits at least one spatial area, wherein all spatial areas purposefully omitted by the switch over signal are intensity minima of an interference pattern and
detecting an optical measurement signal from at least one of the spatial areas purposefully omitted by the switch signal, the substance being selected from a group of substances which is capable of being repeatedly transferred from a first state having first spectral properties to a second state having second spectral properties by means of the switch over signal and which is capable of returning from the second state to the first state, the optical measurement signal being essentially generated by such portions of the substance which have the first but not the second spectral properties.

19. The method of claim 18, wherein the two states are different conformational states of a molecule or a molecule group.

20. The method of claim 18, wherein the substance is selected from the group of substances which may be transferred from the second state to the first state by means of another switching signal.

21. The method of claim 20, wherein the other switching signal is applied to the sample prior to the switch over signal.

22. The method of claim 20, wherein the other switching signal is applied to the sample across all areas which are covered by or purposefully omitted by the switch over signal.

23. The method of claim 18, wherein the first spectral properties as compared to the second spectral properties comprise a distinguishing feature which is selected from:
an increased optical absorption of a probe beam;
an altered polarization property for a probe beam; and
an increased luminescence selected from the group including fluorescence, phosphorescence, electro-luminescence and chemo-luminescence.

24. The method of claim 23, wherein the first spectral properties as compared to the second spectral properties comprise an increased luminescence selected from the group including fluorescence, phosphorescence, electro-luminescence and chemo-luminescence, and wherein an excitation signal is applied to the sample after the switch over signal.

25. The method of claim 24, wherein the excitation signal is applied to the sample across all areas which are covered or purposefully omitted by the switch over signal.

26. The method of claim 23, wherein the first spectral properties as compared to the second spectral properties comprise an increased luminescence selected from the group including fluorescence, phosphorescence, electro-luminescence and chemo-luminescence, and wherein the luminescence is excited by the other switching signal, the other switching signal being applied to the sample during the application of the switch over signal.

27. The method of claim 18, wherein the sample is scanned with the areas purposefully omitted by the switch over signal.

28. The method of claim 18, wherein the substance and the switch over signal are adapted to each other so that everywhere, where the switch over signal exceeds a threshold value essentially the second state of the substance is adjusted.

29. The method of claim 28, wherein the substance and the switch over signals are adapted to each other so that in transfer from the first state to the second state by means of the switch over signal a saturation of the transfer is achieved.

30. The method of claim 18, wherein the substance is selected from the group of substances which includes proteins.

31. The method of claim 18, wherein the substance is selected from the group of substances which includes fluorescent proteins.

32. The method of claim 31, wherein the substance is selected from the group of substances, which includes asCP (asFP595), green-fluorescent protein (GFP), T70a/A148S/S165V an mutants thereof.

33. The method of claim 31, wherein the substance is introduced into a biological sample for marking its structures in an genetic engineering way.

34. The method of claim 18, wherein the method is carried out on a fluorescence microscope after marking the structures with the substance.

35. A method of high spatial resolution imaging a structure of a sample comprising a substance having at least two different states, the method comprising the steps of:
changing the state of the substance by means of an optical switch over signal, which purposefully omits at least one spatial area, and
detecting an optical measurement signal from at least one of the spatial areas purposefully omitted by the switch signal, the substance being selected from a group of substances which is capable of being repeatedly transferred from a first state having first spectral properties to a second state having second spectral properties by means of the switch over signal and which is capable of returning from the second state to the first state, the optical measurement signal being essentially generated by such portions of the substance which have the first but not the second spectral properties,
wherein the substance and the switch over signal are adapted to each other so that everywhere, where the switch over signal exceeds a threshold value essentially the second state of the substance is adjusted.

36. The method of claim 35, wherein the two states are different conformational states of a molecule or a molecule group.

37. The method of claim 35, wherein the substance is selected from the group of substances which may be transferred from the second state to the first state by means of another switching signal.

38. The method of claim 37, wherein the other switching signal is applied to the sample prior to the switch over signal.

39. The method of claim 37, wherein the other switching signal is applied to the sample across all areas which are covered by or purposefully omitted by the switch over signal.

40. The method of claim 35, wherein the first spectral properties as compared to the second spectral properties comprise a distinguishing feature which is selected from:
an increased optical absorption of a probe beam;
an altered polarization property for a probe beam; and
an increased luminescence selected from the group including fluorescence, phosphorescence, electro-luminescence and chemo-luminescence.

41. The method of claim 40, wherein the first spectral properties as compared to the second spectral properties comprise an increased luminescence selected from the group including fluorescence, phosphorescence, electro-luminescence and chemo-luminescence, and wherein an excitation signal is applied to the sample after the switch over signal.

42. The method of claim 41, wherein the excitation signal is applied to the sample across all areas which are covered or purposefully omitted by the switch over signal.

43. The method of claim 40, wherein the first spectral properties as compared to the second spectral properties comprise an increased luminescence selected from the group including fluorescence, phosphorescence, electro-luminescence and chemo-luminescence, and wherein the luminescence is excited by the other switching signal, the other switching signal being applied to the sample during the application of the switch over signal.

44. The method of claim 35, wherein the sample is scanned with the areas purposefully omitted by the switch over signal.

45. The method of claim 35, wherein all spatial areas purposefully omitted by the switch over signal are intensity minima of an interference pattern.

46. The method of claim 35, wherein the substance and the switch over signals are adapted to each other so that in transfer from the first state to the second state by means of the switch over signal a saturation of the transfer is achieved.

47. The method of claim 35, wherein the substance is selected from the group of substances which includes proteins.

48. The method of claim 35, wherein the substance is selected from the group of substances which includes fluorescent proteins.

49. The method of claim 48, wherein the substance is selected from the group of substances, which includes asCP (asFP595), green-fluorescent protein (GFP), T70a/A148S/S165V an mutants thereof.

50. The method of claim 48, wherein the substance is introduced into a biological sample for marking its structures in an genetic engineering way.

51. The method of claim 35, wherein the method is carried out on a fluorescence microscope after marking the structures with the substance.

52. A method of high spatial resolution imaging a structure of a sample comprising a substance having at least two different states, the method comprising the steps of:
changing the state of the substance by means of an optical switch over signal, which purposefully omits at least one spatial area, and
detecting an optical measurement signal from at least one of the spatial areas purposefully omitted by the switch signal, the substance being selected from a group of substances which is capable of being repeatedly transferred from a first state having first spectral properties to a second state having second spectral properties by means of the switch over signal and which is capable of returning from the second state to the first state, the optical measurement signal being essentially generated by such portions of the substance which have the first but not the second spectral properties,
wherein the substance is selected from the group of substances which includes proteins.

53. The method of claim 52, wherein the two states are different conformational states of a molecule or a molecule group.

54. The method of claim 52, wherein the substance is selected from the group of substances which may be transferred from the second state to the first state by means of another switching signal.

55. The method of claim 54, wherein the other switching signal is applied to the sample prior to the switch over signal.

56. The method of claim 54, wherein the other switching signal is applied to the sample across all areas which are covered by or purposefully omitted by the switch over signal.

57. The method of claim 52, wherein the first spectral properties as compared to the second spectral properties comprise a distinguishing feature which is selected from:
an increased optical absorption of a probe beam;
an altered polarization property for a probe beam; and
an increased luminescence selected from the group including fluorescence, phosphorescence, electro-luminescence and chemo-luminescence.

58. The method of claim 57, wherein the first spectral properties as compared to the second spectral properties comprise an increased luminescence selected from the group including fluorescence, phosphorescence, electro-luminescence and chemo-luminescence, and wherein an excitation signal is applied to the sample after the switch over signal.

59. The method of claim 58, wherein the excitation signal is applied to the sample across all areas which are covered or purposefully omitted by the switch over signal.

60. The method of claim 57, wherein the first spectral properties as compared to the second spectral properties comprise an increased luminescence selected from the group including fluorescence, phosphorescence, electro-luminescence and chemo-luminescence, and wherein the luminescence is excited by the other switching signal, the other switching signal being applied to the sample during the application of the switch over signal.

61. The method of claim 52, wherein the sample is scanned with the areas purposefully omitted by the switch over signal.

62. The method of claim 52, wherein all spatial areas purposefully omitted by the switch over signal are intensity minima of an interference pattern.

63. The method of claim 52, wherein the substance and the switch over signal are adapted to each other so that everywhere, where the switch over signal exceeds a threshold value essentially the second state of the substance is adjusted.

64. The method of claim 63, wherein the substance and the switch over signals are adapted to each other so that in transfer from the first state to the second state by means of the switch over signal a saturation of the transfer is achieved.

65. The method of claim 52, wherein the substance is selected from the group of substances which includes fluorescent proteins.

66. The method of claim 65, wherein the substance is selected from the group of substances, which includes asCP (asFP595), green-fluorescent protein (GFP), T70a/A148S/S165V an mutants thereof.

67. The method of claim 48, wherein the substance is introduced into a biological sample for marking its structures in an genetic engineering way.

68. The method of claim 52, wherein the method is carried out on a fluorescence microscope after marking the structures with the substance.

69. A method of high spatial resolution modification of an optical structure, the method comprising the steps of:
providing a structure of a substance having special optical properties, and
changing an optical state of the substance within a spatially limited area by means of an optical writing signal,
wherein the substance is selected from the group of substances which is capable of being repeatedly transferred from a first state having first optical properties to a second state having second optical property by means of an optical switch over signal and which is capable of being returned from the second state to the first state, the spectral state of the substance being changeable by means of the optical writing signal in the first state only, and the second state of the substance being set by means of the switch over signal except for the spatially limited area,
wherein the substance and the switch over signal are adapted to each other so that everywhere where the switch over signal exceeds a threshold value essentially the second state of the substance is adjusted, the spatial area purposefully omitted by the switch over signal being an intensity minimum of an interference pattern.

70. The method of claim 69, wherein the structure is scanned with the spatial areas purposefully omitted by the switch over signal.

71. An optical data storage comprising a structure made of a substance having special optical properties, one optical state of the substance being changeable within a spatially limited area by means of an optical writing signal, the substance belonging to a group of substances which is capable of being repeatedly transferred from a first state having first optical properties to a second state having second optical properties and which is capable of being returned from the second state to the first state, the optical properties of the substance being changeable by means of the optical writing signal in the first state only,
wherein the first spectral properties as compared to the second spectral properties comprise a distinguishing feature which is selected from:
an increased optical absorption of a probe beam;
an altered polarization property for a probe beam; and
an increased luminescence selected from the group including fluorescence, phosphorescence, electro-luminescence and chemo-luminescence.

72. An optical data storage comprising a structure made of a substance having special optical properties, one optical state of the substance being changeable within a spatially limited area by means of an optical writing signal, the substance belonging to a group of substances which is capable of being repeatedly transferred from a first state having first optical properties to a second state having second optical properties and which is capable of being returned from the second state to the first state, the optical properties of the substance being changeable by means of the optical writing signal in the first state only, wherein the substance is selected from the group of substances which includes proteins.

* * * * *

UNITED STATES PATENT AND TRADEMARK OFFICE
CERTIFICATE OF CORRECTION

PATENT NO.        : 7,064,824 B2                                               Page 1 of 1
APPLICATION NO.   : 10/420896
DATED             : June 20, 2006
INVENTOR(S)       : Stefan Hell It is certified that error appears in the above-identified patent and that said Letters Patent is hereby corrected as shown below:

In the title of the patent, change "Resoulution" to --Resolution--, so that the title reads:

High Spatial Resolution Imaging and Modification of Structures

Signed and Sealed this

Twelfth Day of September, 2006

JON W. DUDAS
*Director of the United States Patent and Trademark Office*